United States Patent
Cheng et al.

(10) Patent No.: US 6,365,773 B1
(45) Date of Patent: Apr. 2, 2002

(54) PROCESS FOR PRODUCING FLUOROAROMATIC CARBOXYLATES

(75) Inventors: Chi H. Cheng; Ronny W. Lin, both of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/593,292

(22) Filed: Jun. 13, 2000

(51) Int. Cl.[7] .............................................. C07C 65/00
(52) U.S. Cl. ...................... 562/474; 562/473; 560/406
(58) Field of Search ................. 560/406; 562/474, 562/473

(56) References Cited

U.S. PATENT DOCUMENTS

| | | | | |
|---|---|---|---|---|
| 3,412,162 | A | * | 11/1968 | Rodgerson et al. |
| 5,362,423 | A | * | 11/1994 | IKeda et al. |
| 5,910,605 | A | * | 6/1999 | Cosmo et al. |

FOREIGN PATENT DOCUMENTS

| | | | |
|---|---|---|---|
| GB | 776993 | * | 12/1954 |
| GB | 826620 | * | 11/1956 |
| GB | 1028599 | * | 9/1964 |
| GB | 1027355 | * | 4/1966 |
| GB | 1027356 | | 4/1966 |

OTHER PUBLICATIONS

Barkhash et al., "Preparation and Reactions of Pentafluorophenyl and Pentafluoronapthylmagnesium Chlorides", Doklady Akademi Nauk SSSR, 1964, Ppg. 159, (translated ppg. 1135–1138).

Beck et al., "Direct Conversion of Perfluoroalkanes and Perfluoroarenes to Perfluoro Grignard Reagents", Chem. Commun., 1998, ppg. 693–694.

Harper, Jr., et al., et al., "Reactions of Organometallics With Fluoroaromatic Compounds", J. Org. Chem., 1964, vol. 29, ppg. 2385–2389.

Pearson et al., "The Synthesis of Pentafluorobenzoic Acid and a New Purification of Chloropentafluorobenzene", Synthesis, 1978, vol. 2, ppg. 127.

* cited by examiner

Primary Examiner—Gary Geist
Assistant Examiner—Hector M Reyes
(74) Attorney, Agent, or Firm—Philip M. Pippenger

(57) ABSTRACT

This invention describes processes for producing halomagnesium fluoroaryl carboxylates. In one such process, a fluoroaryl Grignard reagent is added to an anhydrous liquid ethereal medium pretreated with carbon dioxide.

51 Claims, No Drawings ions of fluoroaryl Grignard reagents have been reported. See in this connection U.S. Pat. No. 3,412,162; G.B. Pat. No. 1,027,355; and Vorozhtsov, Jr., et al., *Doklady Akademii Nauk SSSR*, 1964, 159, 125. These are carried out by bubbling carbon dioxide into a solution of the Grignard reagent; yields tend to be low. A higher yield was achieved by Harper et al., *J. Org. Chem.*, 1964, 29, 2385, using solid carbon dioxide, the use of which is not feasible on a commercial scale.

THE INVENTION

This invention makes possible the formation of a fluoroaryl carboxylate from a fluoroaryl Grignard reagent via contact with carbon dioxide in significantly higher yields than was previously possible. Furthermore, this process can be carried out in a commercially feasible, highly efficient manner on a continuous basis.

An embodiment of this invention is a process for producing a halomagnesium fluoroaryl carboxylate. This process comprises adding at least one fluoroaryl Grignard reagent to an anhydrous liquid ethereal medium pretreated with carbon dioxide. The aryl group of the fluoroaryl Grignard reagent is a fluorine-containing aryl group, which has bonded directly to an aromatic ring at least two fluorine atoms, or at least two perfluorohydrocarbyl groups, or at least one fluorine atom and at least one perfluorohydrocarbyl group.

Another embodiment of this invention is a continuous process for producing a halomagnesium fluoroaryl carboxylate. This process comprises continuously and concurrently cofeeding carbon dioxide and at least one fluoroaryl Grignard reagent to a reactor, while periodically or continuously removing product solution from the reactor. The aryl group of the fluoroaryl Grignard reagent is a fluorine-containing aryl group, which has bonded directly to an aromatic ring at least two fluorine atoms, or at least two perfluorohydrocarbyl groups, or at least one fluorine atom and at least one perfluorohydrocarbyl group.

Further embodiments of the invention will be apparent from the ensuing description and appended claims.

The fluoroaryl group of the fluoroaryl Grignard reagent has bonded directly to the aromatic ring at least two fluorine atoms, or at least two perfluorohydrocarbyl groups, or at least one fluorine atom and at least one perfluorohydrocarbyl group. It is preferred that at least two fluorine atoms or at least two perfluorohydrocarbyl groups are bonded directly to the aromatic ring. Each position on the aromatic ring(s) of the fluoroaryl group that is not a fluorine atom or a perfluorohydrocarbyl group is substituted by a hydrogen atom, a hydrocarbyl group, an alkoxy group, or a silyl group.

The halogen atom of the halomagnesium moiety of the fluoroaryl Grignard reagent may be a chlorine atom, bromine atom, or iodine atom. Preferred halogen atoms are chlorine and bromine. Thus, the halomagnesium moiety is preferably a bromomagnesium moiety or a chloromagnesium moiety.

Throughout this document, the term "fluoroaryl group" shall be understood, when not specified, to mean, as described above, a fluorine-containing aryl group, which has bonded directly to an aromatic ring at least two fluorine atoms, or at least two perfluorohydrocarbyl groups, or at least one fluorine atom and at least one perfluorohydrocarbyl group. It is preferred that at least two fluorine atoms or at least two perfluorohydrocarbyl groups are bonded directly to an aromatic ring. Each position on the aromatic ring(s) of the fluoroaryl group that is not a fluorine atom or a perfluorohydrocarbyl group is substituted by a hydrogen atom, a hydrocarbyl group, an alkoxy group, or a silyl group. The aromatic ring of the fluoroaryl group may be, but is not limited to, phenyl, 1-naphthyl, 2-naphthyl, anthryl, biphenylyl, phenanthryl, or indenyl. Phenyl is the preferred aromatic moiety. The perfluorohydrocarbyl substituent groups, when present, include alkyl and aryl perfluorocarbons; suitable perfluorohydrocarbyl groups are, for example, trifluoromethyl, pentafluoroethyl, pentafluorophenyl, and heptafluoronaphthyl. The hydrocarbyl groups of the aryl groups are preferably $C_1$ to $C_{18}$ alkyl groups or $C_6$ to $C_{20}$ aryl or aralkyl groups. Examples of suitable hydrocarbyl groups are methyl, ethyl, isopropyl, tert-butyl, cyclopentyl, methylcyclohexyl, decyl, phenyl, tolyl, xylyl, benzyl, naphthyl, and tetrahydronaphthyl. The alkoxy groups preferably have $C_1$ to $C_6$ alkyl moieties. Some examples of alkoxy groups are methoxy, ethoxy, isopropoxy, methylcyclopentoxy, and cyclohexoxy. The silyl groups preferably have $C_1$ to $C_{18}$ alkyl groups or $C_6$ to $C_{20}$ aryl or aralkyl groups. Suitable silyl groups include trimethylsilyl, triisopropylsilyl, tert-butyl(dimethyl)silyl, tridecylsilyl, and triphenylsilyl. Examples of fluoroaryl groups that can be part of the Grignard reagent in this invention include 3,5-bis(trifluoromethyl)phenyl, 2,4,6-tris(trifluoromethyl)-phenyl, 4-[tri(isopropyl)silyl]-tetrafluorophenyl, 4-[dimethyl(tert-butyl)silyl]-tetrafluorophenyl, 4'-(methoxy)-octafluorobiphenylyl, 2,3-bis(pentafluoroethyl)-naphthyl, 2-(isopropoxy)-hexafluoronaphthyl, 9,10-bis(heptafluoropropyl)-heptafluoroanthryl, 9,10-bis(p-tolyl)-heptafluorophenanthryl, and 1-(trifluoromethyl)-tetrafluoroindenyl. It is preferred that at most two substituents on the ring of the fluoroaryl group are hydrocarbyl, perfluorohydrocarbyl, or alkoxy.

It is highly preferred to have fluoroaryl groups in which all of the substituents are fluorine atoms. Examples of such groups are pentafluorophenyl, 4-nonafluorobiphenylyl, 2-nonafluorobiphenylyl, 1-heptafluoronaphthyl, 2-heptafluoronaphthyl, 7-nonafluoroanthryl, 9-nonafluorophenanthryl, and analogous groups. The most highly preferred perfluoroaryl group is pentafluorophenyl.

Preferred fluoroaryl Grignard reagents include pentafluorophenylmagnesium bromide, heptafluoronaphthylmagnesium chloride, 2-nonafluorobiphenylylmagnesium chloride, 3,5-bis(trifluoromethyl)phenyl bromide, and 2,3-bis(pentafluoroethyl)-naphthylmagnesium chloride. The most highly preferred fluoroaryl Grignard reagents are pentafluorophenylmagnesium bromide and pentafluorophenylmagnesium chloride.

A feature of this invention is pretreatment of a liquid ethereal medium with carbon dioxide prior to the introduction of the fluoroaryl Grignard reagent to the liquid ethereal medium. The liquid ethereal medium that is pretreated with carbon dioxide is comprised of one or more liquid ethers. Any of a variety of monoethers or polyethers may be used, and they may be aliphatic, aromatic, alkylaromatic, and/or cyclic ethers. Examples of ethers that may be used include diethyl ether, ethyl n-propyl ether, di-n-propyl ether, diisopropyl ether, di-n-butyl ether, n-butyl methyl ether, cyclohexyl methyl ether, methoxybenzene, n-butyl phenyl ether, dibenzyl ether, o-xylylene oxide (phthalan), 1,4-benzodioxan, dihydrobenzopyran (chroman), isochroman, trimethylene oxide, 3,3-dimethyltrimethylene oxide, tetrahydrofuran, methyl tetrahydrofuran, tetrahydropyran, 1,4-dioxane, 1,3-dioxane, 1,3-dioxolane, 1,3-dioxepane, glyme (the dimethyl ether of ethylene glycol), diglyme (the dimethyl ether of diethylene glycol), triglyme, and tetraglyme. Unsubstituted cyclic ethers are preferred. Thus, preferred ethers include tetrahydrofuran, tetrahydropyran, 1,3-dioxane, and 1,3-dioxolane. Tetrahydrofuran is an especially preferred liquid ethereal medium in the practice of this invention.

The fluoroaryl Grignard reagent is in a liquid medium. Normally and preferably, this liquid medium is one or more ethers. Ethers in which the fluoroaryl Grignard reagent can be include, for example, those described above for the liquid medium that is pretreated with carbon dioxide. An especially preferred ether for the fluoroaryl Grignard reagent in this invention is tetrahydrofuran. Although not required, the liquid medium in which the fluoroaryl Grignard reagent is dissolved is preferably the same ether or mixture of ethers that is used as the liquid ethereal medium which is pretreated with carbon dioxide.

As is well known in the art, Grignard reagents require anhydrous conditions. Anhydrous conditions are thus necessary for the carboxylation of the fluoroaryl Grignard reagent. The reaction is preferably conducted in an inert atmosphere or, more preferably, in an atmosphere of dry (i.e., anhydrous) carbon dioxide. Another preferred embodiment is the use of mixtures of inert gas(es) and dry carbon dioxide. Inert gases are well known in the art and include, for example, nitrogen, helium, and argon.

Prior to contact with the fluoroaryl Grignard reagent, liquid ethereal medium is pretreated with carbon dioxide. To increase the amount of carbon dioxide in the liquid ethereal medium, the partial pressure of carbon dioxide can be increased. Superior results are achieved at increased pressures; thus, carbon dioxide pressures greater than atmospheric pressure are preferred. Such partial pressures of carbon dioxide are preferably in the range of from about 5 psig to about 100 psig. More preferred are carbon dioxide pressures in the range of from about 20 psig to about 40 psig. It is further preferred that the increased carbon dioxide pressure is maintained throughout the carboxylation reaction.

In one embodiment, the fluoroaryl Grignard reagent is added to the liquid ethereal medium that is pretreated with carbon dioxide. Addition of the fluoroaryl Grignard reagent can be slow (e.g., dropwise), fast, or at intermediate speeds. The rate of addition of the fluoroaryl Grignard reagent does not appear to affect the yield of the reaction. Additional carbon dioxide can be, and preferably is, added concurrently with the addition of the fluoroaryl Grignard reagent. It is also preferred to add additional carbon dioxide during any further mixing time after the addition of the fluoroaryl Grignard reagent is finished.

On the laboratory scale, a preferred contact time for the components of the reaction is in the range of from about five minutes to about six hours. More preferably, the contact time is from about ten minutes to about three hours. Without being bound by theory, it is believed that the reaction of the fluoroaryl Grignard reagent and carbon dioxide is mass transport limited. Thus, if desired, conditions can be optimized so that contact times are quite short (e.g., minutes).

The carboxylation reaction can be conducted in a wide temperature range, so long as the temperature is below the thermal decomposition temperature of the reactants and desired products of the reactions, and the reaction mixtures are in the liquid state under the temperature and pressure conditions being used. Reaction temperatures are often within the range of from about 0° C. to about 60° C. However, temperatures in the range from about −30° C. to about 25° C. usually result in higher yields of the carboxylated product, and temperatures in this range are preferred. More preferred are temperatures in the range of from about −20° C. to about 1° C. Temperatures in the range of from about −20° C. to about 0° C. are highly preferred. Depending on the temperature(s) at which the reaction is conducted, particularly for lower temperatures, care must be taken in the selection of the ether or ethers which comprise the liquid ethereal medium so that the medium is not a solid at the desired reaction temperature.

The halomagnesium fluoroaryl carboxylates produced by this invention can be hydrolyzed to form the corresponding carboxylic acid, or reacted with a metal salt (such as, for example, sodium chloride) to form the desired carboxylate salt.

A further advantage of this invention is that continuous operation is now possible. When initiating continuous operations, liquid ethereal medium pretreated with carbon dioxide is present in the reactor. Fluoroaryl Grignard reagent and carbon dioxide are continuously and concurrently co-fed to the reactor; however, the initiation of such feeds need not be concurrent. When the feed of fluoroaryl Grignard reagent to the reactor is started, or more preferably at some time thereafter, removal of product solution can be initiated. Periodic or continuous removing of product solution, once begun, is preferably maintained continuously and concurrently while fluoroaryl Grignard reagent is being fed. So long as the pressure of carbon dioxide in the reactor is maintained, further addition of liquid ethereal medium pretreated with carbon dioxide is not necessary. Liquid ethereal medium lost by removing product solution is replaced by liquid medium of the fluoroaryl Grignard reagent feed. It is possible to separately feed liquid ethereal medium to the reactor, although such an operation offers no particular advantage. Further, more than one feed of fluoroaryl Grignard reagent and/or carbon dioxide may be used, but again no advantage is gained by doing so. Once the solution has been drained from the reactor, the halomagnesium fluoroaryl carboxylate product can be stored, hydrolyzed, or reacted with a metal salt.

If the reaction is performed in a reactor of sufficient size, the volume of the reactor contents can be cycled between predetermined low and high volumes with initiation of rapid removal when the volume reaches the high volume of reactor contents, and with discontinued removal once the volume reaches the low volume of reactor contents. However, it is preferred to conduct the process so that the volume of the contents of the reactor and portion of the solution removed from the reactor are equal or substantially equal whereby the volume of reactor contents remains constant or substantially constant. In this way, reactors with smaller volumes can be employed.

Thus, once steady-state conditions have been achieved in a continuous reactor, the separate feeds can be fed on a continuous basis, and the reactor contents maintained under the appropriate reaction conditions for virtually unlimited periods of time. Concurrently, a portion of the solution is being removed, usually and preferably continuously, from the reaction mixture so that the volume of the contents of the reactor remains more or less constant.

When operating in a continuous mode and once the continuous feeds have been initiated, the feeds may be adjusted in fine tuning the operation so as to establish and maintain the desired operating conditions for the steady-state operation. Such operation typically can be conducted without mishap for long periods of time before shutdown, e.g., for plant maintenance.

While less preferred, semi-continuous operation is also within the scope of this invention. In semi-continuous operations, fluoroaryl Grignard reagent is fed to at least one and then to at least one other of at least two reactors, which contain anhydrous liquid ethereal medium pretreated with carbon dioxide. While fluoroaryl Grignard reagent is being fed to a reactor, product solution can be, and preferably is, removed from that reactor. Removal of product solution can be initiated when the feed of fluoroaryl Grignard reagent to the reactor containing the medium that is pretreated with carbon dioxide is started, or more preferably at some time thereafter. Most preferably, the solution of fluoroaryl Grignard reagent is being fed continuously or substantially continuously into a reactor containing the medium that is pretreated with carbon dioxide while concurrently and continuously removing a portion of the solution from the reactor. On the laboratory scale, the residence time is typically in the range of from about 25 minutes to about 45 minutes.

In semi-continuous processes, during the time the fluoroaryl Grignard reagent is being fed to at least one of at least two reactors in which there is liquid ethereal medium pretreated with carbon dioxide, additional liquid ethereal medium pretreated with carbon dioxide can be prepared in at least one other of such reactors to which fluoroaryl Grignard reagent is not then being added. In this way, fluoroaryl Grignard reagent can be continuously added to one or more reactors as a continuous feed, while more liquid ethereal medium is pretreated with carbon dioxide in one or more other reactors. Thus, when one reactor is depleted of carbon dioxide, the feed of fluoroaryl Grignard reagent is switched to another reactor which then serves as the receiving reactor for the continuous feed of fluoroaryl Grignard reagent until that reactor is depleted of carbon dioxide, and by that time more of such liquid ethereal medium has been pretreated with carbon dioxide in another reactor. Thus by alternating the production from one reactor (or group of reactors) to another reactor (or group of reactors) and switching back and forth between the reactors, the continuous feed of the fluoroaryl Grignard reagent to liquid ethereal medium pretreated with carbon dioxide can be maintained without material interruption. One way to determine that a reactor has been depleted of liquid ethereal medium pretreated with carbon dioxide is to monitor the carbon dioxide pressure; if it no longer decreases, the carbon dioxide has been depleted.

A particularly preferred embodiment of the above continuous and semi-continuous processes includes the following concurrent operation, namely, continuously withdrawing fluoroaryl Grignard reagent from a reaction vessel, and during the time the fluoroaryl Grignard reagent is being withdrawn from the vessel, forming additional fluoroaryl Grignard reagent in the same reaction vessel. In this way, fluoroaryl Grignard reagent can be continuously withdrawn from a reaction vessel to serve as a continuous feed, while forming more of such fluoroaryl Grignard reagent. Thus, the continuous feed of the fluoroaryl Grignard reagent can be maintained without material interruption.

Another, less preferred embodiment of the above continuous and semi-continuous processes includes the following concurrent operation, namely, continuously, but alternately, withdrawing from at least one and then from at least one other of at least two reaction vessels, fluoroaryl Grignard reagent. During the time the fluoroaryl Grignard reagent is being withdrawn from at least one of at least two such reaction vessels, additional fluoroaryl Grignard reagent is formed in at least one other of such reaction vessels from which solution is not then being withdrawn. In this way, fluoroaryl Grignard reagent can be continuously withdrawn from one or more vessels to serve as a continuous feed, while forming more of such fluoroaryl Grignard reagent in one or more other vessels, so that when one vessel is depleted, the system is switched to another vessel which then serves as the supply for the continuous feed until depleted, and by that time more of such fluoroaryl Grignard reagent has been formed in another vessel. Thus by alternating the supply and the production from one vessel (or group of vessels) to another vessel (or group of vessels) and switching back and forth between the filled vessels as the supply, the continuous feed of the fluoroaryl Grignard reagent can be maintained without material interruption.

Some processes of this invention are continuous or semi-continuous processes and involve continuous feeds. In addition, some embodiments of the invention involve continuous formation of fluoroaryl Grignard reagent. In such embodiments, the term "continuous" or "continuously" is not meant to exclude interrupted feeds. Generally, if such interruptions occur, they are of short duration and are such as not to materially affect the operation of the overall process. An example of such a slight, non-adverse interruption may occur when switching the flow of fluoroaryl Grignard reagent from at least one reactor to another such reactor, an operation which is referred to above as part of a "continuous" feed. As long as such switching operation does not disrupt the operation, such interruption is acceptable and is within the spirit of the term "continuous". Those skilled in the art will of course seek to maintain the continuous feeds with as few interruptions as possible under the given circumstances in which the operation is being conducted.

The term "concurrent" is used in the sense that during substantially the entire reaction period, the designated feeds are being maintained. The use of the term "concurrent" does not exclude the possibility of inconsequential interruptions taking place during the feeds. Nor does this term imply that the feeds must start at exactly the same moment in time. In the case of a co-feed process, the two feeds can be initiated with an interval of time between such initiation as long as the interval is sufficiently short as to cause no material adverse effect upon the overall process. Likewise in the case of a multi-feed operation, there may be one or two different time intervals between or among the respective feeds, again provided that the time intervals are of sufficiently short duration to cause no material adverse effect upon the overall process. Naturally, those skilled in the art will strive to utilize the concurrent feeds with as little nonconcurrence as possible.

It should be understood that while the concurrent feeds are preferably continuous concurrent feeds, slight interruptions in a feed are acceptable provided that the duration of the interruption is sufficiently small as to cause no material disruption in the reaction. Thus as used herein, the terms "concurrent" and "continuous" should be understood to embrace the minor departures just referred to.

The fluoroaryl Grignard reagent can be made by reacting either magnesium metal or a hydrocarbyl Grignard reagent with a fluoroaromatic compound which has a chlorine atom, a bromine atom, or an iodine atom directly bonded to an aromatic ring of the compound. Other substituents for the fluoroaromatic compound are as described above for the fluoroaryl groups of the fluoroaryl Grignard reagent. That is, directly bonded to an aromatic ring are at least two fluorine atoms, or at least two perfluorohydrocarbyl groups, or at least one fluorine atom and at least one perfluorohydrocarbyl group. Each position on the aromatic ring(s) of the fluoroaryl group that is not a chlorine atom, a bromine atom, or an iodine atom, or a fluorine atom or a perfluorohydrocarbyl group, is a hydrogen atom, a hydrocarbyl group, an alkoxy group, or a silyl group. Examples of suitable fluoroaromatic compounds include, but are not limited to, chloropentafluorobenzene, bromopentafluorobenzene, 1-chloro-2,4,6-tris(trifluoromethyl)-benzene, 1-bromo-2-(isopropoxy)-hexafluoronaphthalene, and 1-chloro-9,10-bis (heptafluoropropyl)-heptafluoroanthracene. The most highly preferred fluoroaromatic compound is chloropentafluorobenzene. It is preferred to use magnesium metal in the reaction with the fluoroaromatic compound.

Forms of magnesium metal that can be used in the reaction to make the fluoroaryl Grignard reagent include turnings, powder, chips, granules, and the like. The preferred form of magnesium metal in this invention is granules. When magnesium metal is used, it is preferably in molar excess of the amount of fluoroaromatic compound used. The preferred molar ratio is in the range of from about 1.01 mole of magnesium metal per mole of fluoroaromatic compound to about 2.0 moles of magnesium metal per mole of fluoroaromatic compound. Most desirable is a molar ratio of about 1.15 to about 1.5 mole magnesium metal per mole fluoroaromatic compound.

For the hydrocarbyl Grignard reagent used to make the fluoroaryl Grignard reagent, the word hydrocarbyl is defined as any monovalent group derived from a linear, branched, or cyclic $C_1$ to $C_{20}$ hydrocarbon. Examples of hydrocarbyl Grignard reagents include ethylmagnesium chloride, sec-butylmagnesium bromide, cyclopentenylmagnesium chloride, cyclohexylmagnesium bromide, 3-hexenylmagnesium iodide, 4-methylcyclooctylmagnesium iodide, 6-ethyldodecylmagnesium bromide, and eicosylmagnesium chloride. Short-chain alkyl Grignard reagents, e.g., $C_1$ to $C_6$, are preferred hydrocarbyl Grignard reagents, and the preferred halogen atom of the hydrocarbyl Grignard reagent is a bromine atom. Ethylmagnesium bromide is the most highly preferred hydrocarbyl Grignard reagent.

When a hydrocarbyl Grignard reagent is used to make the fluoroaryl Grignard reagent, it is preferably in molar excess of the amount of fluoroaromatic compound used. The preferred molar excess of hydrocarbyl Grignard reagent is in the range of from about 1.01 mole of hydrocarbyl Grignard reagent per mole of fluoroaromatic compound to about 1.2 mole of hydrocarbyl Grignard reagent per mole fluoroaromatic compound. Most desirable is a molar excess of about 1.05 to about 1.15 mole of hydrocarbyl Grignard reagent per mole of fluoroaromatic compound.

The following examples are presented for purposes of illustration, and are not intended to impose limitations on the scope of this invention.

GENERAL PROCEDURES

Reagents. Magnesium granules were obtained from Reade Manufactory Company, carbon dioxide (bone dry, minimum 99.8%) was obtained from Matheson Tri-Gas Incorporated, and chloropentafluorobenzene was obtained from Chordip Limited. Chloropentafluorobenzene and all solvents used in the Grignard reactions and carboxylation reactions were dried over molecular sieves for at least 24 hours.

Conditions. All reactions were carried out in a nitrogen purged glove box, and all reactions were stirred.

EXAMPLE 1

Ethylmagnesium bromide in diethyl ether (10.13 g, 3.0 moles per liter, 0.0298 mol) and diethyl ether (33.68 g) were charged to a 100 mL round bottom flask. Chloropentafluorobenzene (5.13 g, 0.02533 mol) was then slowly pipetted into the flask. The temperature of the reaction mixture was maintained at 30–40° C. After 3 hours, a sample of the reaction mixture was analyzed by gas chromatography, which showed that 95% of the chloropentafluorobenzene was still unreacted. Tetrahydrofuran (9.7 g) was then added to the reaction mixture. Thirty minutes after the tetrahydrofuran addition, the yield of pentafluorophenylmagnesium bromide was 34%; 3 hours after the tetrahydrofuran addition, the yield of pentafluorophenylmagnesium bromide was 77%.

EXAMPLE 2

Chloropentafluorobenzene 4.98 g (0.0246 mol) and tetrahydrofuran (23.47 g) were charged to a 100 mL round bottom flask. Ethylmagnesium bromide in tetrahydrofuran (27.13 g, 1.0 moles per liter, 0.0266 mol) was charged to a dropping funnel and then slowly added to the flask during 1.5 hours while maintaining the temperature of the reaction mixture at 25–38° C. Large exotherms and gas evolution were observed. The product solution, containing pentafluorophenylmagnesium bromide, was transferred to a 100 mL dropping funnel.

A jacketed 250 mL round bottom flask was charged with tetrahydrofuran (120.2 g). The flask was cooled to –10° C., and then continuous bubbling of carbon dioxide was initiated. The pentafluorophenylmagnesium bromide solution was added slowly during one hour, while maintaining the temperature of the reaction mixture at –10° C. The bubbling of carbon dioxide was then stopped, and the reaction mixture was allowed to warm to room temperature. The reaction mixture was then hydrolyzed with aqueous HCl (9.3 g, 15.8 wt %), and extracted with diethyl ether (47.8 g). The ethereal solution was analyzed by NMR, and found to contain chloropentafluorobenzene (0.0045 mol) and pentafluorophenylcarboxylic acid (3.66 g, 0.017 mol), a yield of 86% based on the amount of chloropentafluorobenzene reacted.

EXAMPLE 3

Magnesium granules (1.05 g, 0.0432 mol) and tetrahydrofuran (29.4 g) were charged to a 100 mL round bottom flask. Chloropentafluorobenzene (5.62 g, 0.0277 mol) was charged to a dropping funnel and then slowly added to the flask. When about 0.93 g of chloropentafluorobenzene had been added, the reaction mixture turned dark, and an exotherm was observed. While the remainder of the chloropentafluorobenzene was added, the temperature rose to about 65° C. After the chloropentafluorobenzene addition was finished, the reaction mixture was stirred for another 10 minutes at 47–55° C. Gas chromatography of a sample from the mixture showed that the reaction was complete. The product solution, containing pentafluorophenylmagnesium chloride, was transferred to a dropping funnel.

The pentafluorophenylmagnesium chloride was reacted with carbon dioxide as described for pentafluorophenylmagnesium bromide in Example 2 except that the addition time was 25 minutes, the amount of tetrahydrofuran was 98.62 g, and 17.94 g (10.5 wt %) aqueous HCl was used for the hydrolysis. The ethereal solution was analyzed by NMR, and found to contain pentafluorophenylcarboxylic acid (4.65 g, 0.0219 mol), a yield of 79% based on the amount of chloropentafluorobenzene used.

The ethereal phase was concentrated to 20.11 g via evaporation, and aqueous sodium hydroxide (42.0 g, 4 wt %) was added to the ethereal phase. Diethyl ether (34.6 g) was added to the two-phase mixture. The aqueous phase of the two-phase mixture was acidified with aqueous HCl (4.24 g, 36 wt % 1), and then washed twice with diethyl ether. After the phases were separated, the ethereal phase was evaporated to dryness, yielding 4.2 g of solid. The solid contained 90.7% pentafluorophenylcarboxylic acid, as determined by NMR, a 65% isolated yield based on the amount of chloropentafluorobenzene used.

EXAMPLE 4

Pentafluorophenylmagnesium chloride was made in the same manner as described in Example 3. The amounts of reagents used were as follows: magnesium granules, 1.76 g, (0.0724 mol); tetrahydrofuran, 54.0 g; and chloropentafluorobenzene 10.28 g (0.05076 mol). When 1.7 mL of the chloropentafluorobenzene had been added, the reaction mixture turned dark, and an exotherm was observed. The mixture was cooled to 10° C., and maintained at that temperature during the rest of the chloropentafluorobenzene addition (10 more minutes) and for an additional 20 minutes. Gas chromatography of a sample from the mixture showed that the reaction was complete. The product solution, containing pentafluorophenylmagnesium chloride, was then suction transferred into a pre-evacuated bomb, which was then pressurized to 50 psig using helium.

A 300 mL stainless steel autoclave was charged with tetrahydrofuran (149.2 g). All of the inert gases were removed by 3 cycles of pressurizing with carbon dioxide and venting. The autoclave was then pressurized to 22 psig with carbon dioxide and cooled to −10° C. During the reaction, the vapor space of the reactor was continuously purged through a bubbler to ensure that there was no buildup of inert gases. The pentafluorophenylmagnesiurn chloride solution was added slowly during 20 minutes from the bomb to the autoclave via a needle valve, while maintaining the temperature of the mixture in the autoclave at −10° C. and the (carbon dioxide) pressure in the autoclave at 22 psig. When the addition was finished, the pressure in the autoclave was released (to atmospheric pressure), and the mixture in the autoclave was allowed to warm to room temperature.

The mixture from the autoclave was concentrated under partial vacuum (25 mmHg) at 26° C. on arotary evaporator. The distillate (181 g) contained 0.109 g of pentafluorobenzene, as determined by NMR. The thick bottoms material (22.3 g) was hydrolyzed with aqueous HCl (20.66 g, 9.5 wt %), and extracted with toluene (88.5 g). The toluene solution was analyzedby $^{19}$F NMR, and found to containpentafluorophenylcarboxylic acid (10.22 g, 0.0482 mol), a yield of 96% based on the amount of chloropentafluorobenzene used. No other fluorinated compounds were observed in the $^{19}$F NMR spectrum.

EXAMPLE 5

Pentafluorophenylcarboxylic acid was made as described in Example 4. For the synthesis of pentafluorophenylmagnesium chloride, the amounts of reagents used were: magnesium granules, 1.76 g, (0.0724 mol); tetrahydrofuran, 53.2 g; and chloropentafluorobenzene 10.04 g (0.04958 mol). The dark color and the exotherm were observed after 1.3 mL of chloropentafluorobenzene had been added. For the synthesis of chloromagnesium pentafluorophenylcarboxylate, 157.8 g of tetrahydrofuran were added to the autoclave; the autoclave was pressurized to 45 psig with carbon dioxide just prior to the start of the pentafluorophenylmagnesium chloride addition; the carbon dioxide pressure during the reaction was 38 psig; and the addition time for the pentafluorophenylmagnesium chloride solution to the solution in the autoclave was 15 minutes.

The product mixture in the autoclave, which contained chloromagnesium pentafluorophenylcarboxylate, was mixed with toluene (124.4 g) and distilled at atmospheric pressure using a 12-inch column packed with 0.25-inch stainless steel packing (Pro-Pak®, Ace Glass Incorporated, Vineland, N.J.). The bottoms material (84.3 g) was hydrolyzed with aqueous HCl (22 g, 9.4 wt %), and extracted with toluene (10.5 g). The toluene solution was analyzed by $^{19}$F NMR, and found to contain pentafluorophenylcarboxylic acid (9.57 g, 0.04154 mol), a yield of 92% based on the amount of chloropentafluorobenzene used. No other fluorinated compounds were observed in the $^{19}$F NMR spectrum.

The toluene solution (84.5 g) was concentrated by evaporation at atmospheric pressure at 110° C. to about 44.6 g. The solution was then cooled to −10° C., precipitating pentafluorophenylcarboxylic acid, which was filtered, washed with ice water, and dried in vacuo at 65° C. The solid pentafluorophenylcarboxylic acid (5.22 g, 0.0246 mol) contained 99.6% pentafluorophenylcarboxylic acid and 0.02% toluene. The mother liquor contained 2.6 g of pentafluorophenylcarboxylic acid (0.01226 mol).

EXAMPLE 6

Pentafluorophenylcarboxylic acid was made as described in Example 5. For the synthesis of pentafluorophenylmagnesium chloride, the amounts of reagents used were: magnesium granules, 1.76 g, (0.0724 mol); tetrahydrofuran, 52.9 g; and chloropentafluorobenzene 9.97 g (0.0492 mol). The dark color and the exotherm were observed after 1.3 mL of chloropentafluorobenzene had been added; the addition time for the rest of the chloropentafluorobenzene was 22 minutes. For the synthesis of chloromagnesium pentafluorophenylcarboxylate, 122.4 g of tetrahydrofuran were added to the autoclave; the pressure used for the 3 cycles of pressurizing was 40 psig; the autoclave was pressurized to 38 psig with carbon dioxide just prior to the start of the pentafluorophenylmagnesium chloride addition; the carbon dioxide pressure during the reaction was 38 psig; and the addition time for the pentafluorophenylmagnesiun chloride solution to the solution in the autoclave was 32 minutes.

Tetrahydrofuran was evaporated from the product mixture from the autoclave. The rest of the workup described in Example 5 was then followed. The amount of toluene added was 199.1 g; 155.2 g of bottoms materials were obtained; aqueous HCl (25 g, 8.9 wt %) was used for the hydrolysis; and 13.1 g of toluene were used for the extraction. The $^{19}$F NMR analysis found pentafluorophenylcarboxylic acid (9.52 g, 0.0449 mol), a yield of 93.6% based on the amount of chloropentafluorobenzene used. No other fluorinated compounds were observed in the $^{19}$F NMR spectrum. The solid pentafluorophenylcarboxylic acid (6.56 g, 0.03094 mol), obtained in an isolated yield of 62%, contained 99.8% pentafluorophenylcarboxylic acid, and 0.03% toluene. The mother liquor contained about 1.95 g of pentafluorophenylcarboxylic acid (0.0092 mol).

The mother liquor was concentrated by evaporation at atmospheric pressure at 110° C., and then cooled to –10° C., precipitating more pentafluorophenylcarboxylic acid, which was filtered, washed with ice water, and dried in vacuo. Another 1.29 g of pentafluorophenylcarboxylic acid was obtained; about 0.454 g of pentafluorophenylcarboxylic acid still remained in the mother liquor.

EXAMPLE 7

Pentafluorophenylcarboxylic acid was made as described in Example 5. For the synthesis of pentafluorophenyhnagnesium chloride, the amounts of reagents used were: magnesium granules, 1.75 g, (0.072 mol); tetrahydrofuran, 53.45 g; and chloropentafluorobenzene 10.03 g (0.0495 mol). The dark color and the exotherm were observed after 0.8 mL of chloropentafluorobenzene had been added; the addition time for the rest of the chloropentafluorobenzene was 17 minutes. For the synthesis of chloromagnesium pentafluorophenylcarboxylate, 125.4 g of tetrahydrofuran were added to the autoclave; the pressure used for the 3 cycles of pressurizing was 40 psig; the autoclave was pressurized to 38 psig with carbon dioxide just prior to the start of the pentafluorophenylmagnesium chloride addition; the carbon dioxide pressure during the reaction was 38 psig; and the addition time for the pentafluorophenylmagnesium chloride solution to the solution in the autoclave was 20 minutes.

Tetrahydrofuran was evaporated from the product mixture from the autoclave. The rest of the workup described in Example 5 was then followed. The amount of toluene added was 86 g; 115.3 g of bottoms materials were obtained; aqueous HCl (29 g, 7.1 wt %) was used for the hydrolysis; and 47.9 g of toluene were used for the extraction. The 19F NMR analysis found pentafluorophenylcarboxylic acid (9.76 g, 0.046 mol), a yield of 95% based on the amount of chloropentafluorobenzene used. No other fluorinated compounds were observed in the $^{19}$F NMR spectrum.

The crystallized pentafluorophenylcarboxylic acid was washed with cold toluene (46 g) instead of water, and dried at 60° C. The solid pentafluorophenylcarboxylic acid (8.15 g, 0.03844 mol), obtained in an isolated yield of 82%, had a purity of 99.8%. The mother liquor contained about 1.152 g of pentafluorophenylcarboxylic acid (0.00544 mol).

EXAMPLE 8

The formation of the fluoroaromatic Grignard reagent and the carboxylation of the Grignard reagent were carried out in a continuous mode in two consecutive stirred reactors.

Magnesium granules (13.7 g, 0.564 mol) and tetrahydrofuran (104.7 g) were charged to a 300 mL Pyrex jacketed reaction kettle equipped with a stir bar and a thermowell. The stirring rate was adjusted so that most of the magnesium granules were suspended in the bottom half of the liquid volume.

A 300 mL stainless steel autoclave equipped with a magnetic drive agitator, thermowell, pressure gauge, and an external cooling bath was charged with tetrahydrofuran (1 32.4 g). All of the inert gases were removed by 3 cycles of pressurizing with carbon dioxide and venting. The autoclave was then pressurized to 22 psig with carbon dioxide and cooled to –10° C.

A solution of chloropentafluorobenzene (95.18 g, 0.47 mol) in tetrahydrofuran (882 g) was fed using a metering pump at a rate of 5 mL per minute to a dip leg located near the stir bar of the kettle. When the reaction mixture turned dark, the reactor was cooled to, and then maintained at, 10° C.

When the liquid volume of the kettle reached 175 mL, the solution in the kettle was continuously fed, using a metering pump, from a dip leg located just below the top of the liquid level in the kettle into the vapor space of the autoclave, while maintaining the temperature of the mixture in the autoclave at –10° C., and the (carbon dioxide) pressure in the autoclave at 22 psig. The solution of the carboxylated product was continuously discharged using a metering pump from a dip leg of the autoclave into a one gallon collecting flask, where the pressure was released (to atmospheric pressure), and the solution was allowed to warm to room temperature. A total of 1174.1 g of solution was obtained. About 0.0177 mol of Grignard compounds remained behind in the reactor (s) and/or apparatus.

A portion of the product solution (194.6 g, 0.075 mol of chloromagnesium pentafluorophenylcarboxylate) was separated from the main bulk of the product solution. The tetrahydrofuran was evaporated from this portion, and then the portion was hydrolyzed with aqueous HCl (39.4 g, 10.3 wt %), and extracted twice with toluene (182 g). The toluene extractions were combined, and the toluene solution was distilled at atmospheric pressure using a 12-inch column packed with 0.25-inch stainless steel packing (Pro-Pak®). The resultant concentrated solution was cooled to –10° C., precipitating pentafluorophenylcarboxylic acid, which was filtered, washed with cold toluene (38 g), and dried under vacuum at 60° C. The solid pentafluorophenylcarboxylic acid (11.88 g, 0.056 mol) contained 99.8% pentafluorophenylcarboxylic acid and 0.03% toluene. The mother liquor contained about 2.18 g of pentafluorophenylcarboxylic acid (0.0103 mol).

Two other workups were attempted, but these were significantly less successful than the workup just described.

COMPARATIVE EXAMPLE 1

Ethylmagnesium bromide in tetrahydrofuran (29.66 g, 1.0 moles per liter, 0.0294 mol) was charged to a 100 mL round bottom flask. Chloropentafluorobenzene (5.00 g, 0.0247 mol) was then slowly pipetted into the flask. Large exothetms and gas evolution were observed; the temperature of the mixture rose to about 60° C. The mixture was analyzed by gas chromatography, which showed that all of the chloropentafluorobenzene had been converted to pentafluorophenylmagnesium bromide.

The mixture was then cooled to 30° C. and maintained at this temperature. Gaseous carbon dioxide was bubbled into the mixture until gas breakthrough of carbon dioxide and no exotherms were observed. This mixture was hydrolyzed with aqueous HCl (23.4 g, 9 wt %), and then extracted with a mixture of diethyl ether (26.3 g) and tetrahydrofuran (31.5 g). White solids (impurities and/or byproducts) were observed. The ethereal solution was analyzed by NMR, and found to contain pentafluorophenylcarboxylic acid (2.0 g, 0.0094 mol), a yield of 38% based on the amount of chloropentafluorobenzene used.

COMPARATIVE EXAMPLE 2

Pentafluorophenylmagnesium bromide was made in the same manner as described in Comparative Example 1. The amounts of reagents used was as follows: chloropentafluorobenzene, 5.24 g, (0.0259 mol); tetrahydrofuran 23.3 g; ethylmagnesium bromide in tetrahydrofuran, 27.38 g (1.0 moles per liter, 0.0271 mol). The addition time for the ethylmagnesium bromide was 35 minutes; the temperature was maintained at 30 to 40° C.

After an additional 20 minutes, gaseous carbon dioxide was bubbled into the reaction mixture for 2 hours while maintaining the temperature of the reaction mixture at about 30° C. This mixture was hydrolyzed with aqueous HCl (5.2 g, 35 wt %), and then extracted with diethyl ether (38.1 g). White solids (impurities and/or byproducts) were observed. The ethereal solution was analyzed by NMR, and found to contain pentafluorophenylcarboxylic acid (2.1 g, 0.0094 mol), a yield of 39% based on the amount of chloropentafluorobenzene used.

COMPARATIVE EXAMPLE 3

Pentafluorophenylmagnesium chloride was made as described in Example 4, except that the stirring time after the end of the chloropentafluorobenzene addition was 10 minutes. The product solution of pentafluorophenylmagnesium chloride was transferred to a 500 mL round bottom flask and cooled to −10° C. Gaseous carbon dioxide was bubbled into the solution for 1 hour while maintaining the temperature of the solution at −10° C. When the bubbling was finished, the solution was allowed to warm to room temperature, and was concentrated under partial vacuum (25 mmHg) at 26° C. on a rotary evaporator. The thick bottoms material (22.31 g) was then hydrolyzed with aqueous HCl (21.32 g, 9.8 wt %), and extracted with toluene (93.7 g). A large amount of white solids (impurities and/or byproducts) were observed. The toluene solution was analyzed by $^{19}$F NMR, and found to contain pentafluorophenylcarboxylic acid (6.64 g, 0.03132 mol), a yield of 62% based on the amount of chloropentafluorobenzene used.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

It will also be understood that the terms "substantial" and "substantially" denote that chemical processes ordinarily do not involve absolutes. Thus instead of describing a variable as an absolute, it is far more realistic to describe the variable as being in the substantial vicinity of the expressed variable. For example when describing a stoichiometric quantity it is far more realistic to refer to the quantity as being substantially a stoichiometric quantity since one skilled in the art fully realizes that slight deviations from the absolute stoichiometry would produce no appreciable difference in results. Thus in any and all respects, this document should be read with the application of common sense.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises adding to an anhydrous liquid ethereal medium that has been pretreated with and that contains carbon dioxide, at least one fluoroaryl Grignard reagent, wherein the aryl group is a fluorine-containing aryl group, which has bonded directly to an aromatic ring at least two fluorine atoms, or at least two perfluorohydrocarbyl groups, or at least one fluorine atom and at least one perfluorohydrocarbyl group, to produce a halomagnesium fluoroaryl carboxylate.

2. A process according to claim 1 wherein the halomagnesium moiety of said Grignard reagent is comprised of either a chloromagnesium moiety or a bromomagnesium moiety.

3. A process according to claim 1 wherein the aromatic ring of said aryl group is a phenyl ring.

4. A process according to claim 3 wherein said aryl group is a pentafluorophenyl group.

5. A process according to claim 4 wherein said Grignard reagent is either pentafluorophenylmagnesium bromide or pentafluorophenylmagnesium chloride.

6. A process according to claim 1 wherein all of the substituents selected from fluorine atoms or perfluorinated hydrocarbyl groups are fluorine atoms.

7. A process according to claim 6 wherein all of the substituents on the aromatic ring(s) are fluorine atoms.

8. A process according to claim 1 wherein said liquid ethereal medium is comprised of a cyclic ether.

9. A process according to claim 8 wherein said cyclic ether is comprised of tetrahydrofuran.

10. A process according to claim 1 wherein said process is conducted with the temperature of said medium being in the range of from about −30° C. to about 25° C.

11. A process according to claim 1 wherein the anhydrous liquid ethereal medium is maintained under a carbon dioxide pressure in the range of from about 5 psig to about 100 psig.

12. A process according to claim 10 wherein the anhydrous liquid ethereal medium is maintained under a carbon dioxide pressure in the range of from about 5 psig to about 100 psig.

13. A process according to claim 1 wherein additional carbon dioxide is added during said process.

14. A process according to claim 1 wherein said liquid ethereal medium is comprised of tetrahydrofuran, wherein said fluoroaryl Grignard reagent is either pentafluorophenylmagnesium bromide or pentafluorophenylmagnesium chloride, and wherein said process is conducted with the temperature of said medium being in the range of from about −30° C. to about 25° C.

15. A process according to claim 14 wherein the anhydrous liquid ethereal medium is maintained under a carbon dioxide pressure in the range of from about 5 psig to about 100 psig.

16. A process according to claim 14 wherein additional carbon dioxide is added during said process.

17. A process according to claim 1 wherein said process comprises feeding said fluoroaryl Grignard reagent to at least one reactor in which there is an anhydrous liquid ethereal medium pretreated with carbon dioxide; and wherein, when said reactor is depleted of carbon dioxide, switching said feeding of fluoroaryl Grignard reagent to another at least one reactor in which there is an anhydrous liquid ethereal medium pretreated with carbon dioxide.

18. A process according to claim 17 wherein the feeding of the fluoroaryl Grignard reagent is continuous or substantially continuous.

19. A process according to claim 17 wherein, while feeding said fluoroaryl Grignard reagent, product solution is drained from said reactor.

20. A process according to claim 19 wherein said removing is continuous or substantially continuous.

21. A process according to claim 17 wherein the aromatic ring of said aryl group is a phenyl ring.

22. A process according to claim 17 wherein all of the substituents on the aromatic ring(s) are fluorine atoms.

23. A process according to claim 21 wherein said Grignard reagent is either pentafluorophenylmagnesiumn bromide or pentafluorophenylmagnesium chloride.

24. A process according to claim 17 wherein said liquid ethereal medium is comprised of a cyclic ether.

25. A process according to claim 24 wherein said cyclic ether is comprised of tetrahydrofuran.

26. A process according to claim 17 wherein said process is conducted with the temperature of said medium being in the range of from about −30° C. to about 25° C.

27. A process according to claim 17 wherein the anhydrous liquid ethereal medium is maintained under a carbon dioxide pressure in the range of from about 5 psig to about 100 psig.

28. A process according to claim 17 wherein said liquid ethereal medium is comprised of tetrahydrofuran, wherein said fluoroaryl Grignard reagent is either pentafluorophenylmagnesium bromide or pentafluorophenylmagnesium chloride, and wherein said process is conducted with the temperature of said medium being in the range of from about −30° C. to about 25° C. and said medium being under a carbon dioxide pressure in the range of from about 5 psig to about 100 psig.

29. A process according to claim 28 wherein the feeding of the fluoroaryl Grignard reagent is continuous or substantially continuous.

30. A process for producing a halomagnesium fluoroaryl carboxylate which comprises continuously and concurrently cofeeding to a reactor containing an anhydrous liquid ethereal medium, (i) carbon dioxide and (ii) at least one fluoroaryl Grignard reagent, wherein the aryl group of said fluoroaryl Grignard reagent is a fluorine-containing aryl group, which has bonded directly to an aromatic ring at least two fluorine atoms, or at least two perfluorohydrocarbyl groups, or at least one fluorine atom and at least one perfluorohydrocarbyl group, while periodically or continuously removing product solution from said reactor, said medium having been pretreated with and containing carbon dioxide prior to the initiation of the feeding of said at least one fluoroaryl Grignard reagent.

31. A process according to claim 30 wherein additional fluoroaryl Grignard reagent is continuously formed in a separate vessel and withdrawn from said vessel for said cofeeding.

32. A process according to claim 30 wherein said removing is continuous or substantially continuous.

33. A process according to claim 30 wherein the halomagnesium moiety of said Grignard reagent is comprised of either a chloromagnesium moiety or a bromomagnesium moiety.

34. A process according to claim 30 wherein the aromatic ring of said aryl group is a phenyl ring.

35. A process according to claim 34 wherein said aryl group is a pentafluorophenyl group.

36. A process according to claim 35 wherein said Grignard reagent is either pentafluorophenylmagnesium bromide or pentafluorophenylmagnesium chloride.

37. A process according to claim 30 wherein all of the substituents selected from fluorine atoms or perfluorinated hydrocarbyl groups are fluorine atoms.

38. A process according to claim 37 wherein all of the substituents on the aromatic ring(s) are fluorine atoms.

39. A process according to claim 30 wherein said liquid ethereal medium is comprised of a cyclic ether.

40. A process according to claim 39 wherein said cyclic ether is comprised of tetrahydrofuran.

41. A process according to claim 30 wherein said cofeeding is conducted with the temperature of said medium being in the range of from about −30° C. to about 25° C.

42. A process according to claim 30 wherein the carbon dioxide pressure in said reactor is in the range of from about 5 psig to about 100 psig.

43. A process according to claim 41 wherein the carbon dioxide pressure in said reactor is in the range of from about 5 psig to about 100 psig.

44. A process according to claim 30 wherein said liquid ethereal medium is comprised of tetrahydrofuran, wherein said fluoroaryl Grignard reagent is either pentafluorophenylmagnesium bromide or pentafluorophenylmagnesium chloride, and wherein said cofeeding is conducted with the temperature of said medium being in the range of from about −30° C. to about 25° C.

45. A process according to claim 44 wherein the carbon dioxide pressure in said reactor is in the range of from about 5 psig to about 100 psig.

46. A process according to claim 44 wherein said removing is continuous or substantially continuous.

47. A process according to claim 44 wherein additional fluoroaryl Grignard reagent is continuously formed in a separate vessel and withdrawn from said vessel for said cofeeding.

48. A process according to claim 47 wherein the carbon dioxide pressure in said reactor is in the range of from about 5 psig to about 100 psig.

49. A process according to any of claims 11, 12, 15, 27, 28, 42, 43, 45, or 48 wherein said carbon dioxide pressure is in the range of from about 20 psig to about 40 psig.

50. A process according to any of claims 10, 14, 26, 28, 41, or 44 wherein said temperature is in the range of from about −20° C. to about 10° C.

51. A process according to claim 28 wherein said temperature is in the range of from about −20° C. to about 10° C., and said carbon dioxide pressure is in the range of from about 20 psig to about 40 psig.

* * * * *